United States Patent [19]

Snider

[11] Patent Number: 4,952,211

[45] Date of Patent: Aug. 28, 1990

[54] FEMININE TAMPON COATED WITH BEESWAX

[76] Inventor: Dale Snider, 3404 Leigh Rd., Pompano Beach, Fla. 33062

[21] Appl. No.: 242,639

[22] Filed: Sep. 12, 1988

[51] Int. Cl.$^5$ .............................................. A61F 13/20
[52] U.S. Cl. .................................. 604/285; 604/358; 604/904
[58] Field of Search .............. 604/358, 365, 382, 330, 604/285, 363, 904, 287

[56] References Cited

U.S. PATENT DOCUMENTS

| 3,512,527 | 10/1967 | Desoye et al. | 604/285 X |
| 3,796,219 | 3/1974 | Hanke | 604/904 X |
| 4,029,113 | 6/1977 | Guyton | 132/321 |

FOREIGN PATENT DOCUMENTS

| 116357 | 1/1943 | Australia | 604/363 |
| 860911 | 11/1971 | Canada | 604/363 |
| 975872 | 11/1964 | United Kingdom | 604/363 |

Primary Examiner—Richard J. Apley
Assistant Examiner—Rachel M. Healey
Attorney, Agent, or Firm—M. K. Silverman

[57] ABSTRACT

Disclosed is an improved tampon having a longitudinal circumferential coating of beeswax of the *Apis mellifera* species.

7 Claims, No Drawings

FEMININE TAMPON COATED WITH BEESWAX

BACKGROUND OF THE INVENTION

The present invention is directed to a novel structure for a feminine tampon and, as well, a method for forming the same. The invention, more particularly, relates to a unique coating for an otherwise conventional tampon which, thereby, will reduce the release of fibers from the tampon and resultingly, will remove from the tampon a means by which bacteria is transported from the vagina to the uterus and the entire system of the user More particularly, the medical literature has recognized a correlation between the use of tampons containing high absorbency materials and increased incident of Toxic Shock Syndrome (TSS) and other conditions. See for example "The Incidence of Toxic Shock Syndrome in Northern California. 1972 thru 1983" by Petitti, Reingold, and Chin, Journal of the American Medical Association, 1986, 255 (3); "A review of the Epidemiologic studies of Toxic Shock Syndrome," by Stallones, Internal Medicine Annual, 1982 June 96 (6 PT 2).; "The Toxic Shock Syndrome Revisited" by Kass, Postgraduate Medical Journal, (1985) 61 (Suppl. 1); and "Effects of Tampon Materials on the Invitro Physiology of Toxic Shock Syndrome Strain of Staphylococcus Aureus", by Ingham, Eady, Holland, and Gowland, Medical Micro biology, Volume 20 (1985) 87–95.

The above are but representative of the many publications which exist that have suggested a relationship between the use of tampons and the incidence of TSS which, more particularly, have suggested that the more absorbent the tampon, the greater is the occurrence of TSS.

The present invention may, accordingly, be viewed as a response to the above problems associated with high absorbency tampons and, more particularly, may be viewed as an attempt to provide a tampon of suitable absorbency which will not have associated therewith the problem of fiber release evidenced in prior art tampons.

The inventor is unaware of any prior art patents which address the above problem or which are otherwise relevant to the invention as set forth herein.

SUMMARY OF THE INVENTION

The present invention comprises a method of coating an otherwise conventional fiber fabric tampon with a coating of beeswax from the European honeybee (*Apis mellifera*). The coating of beeswax may be in the range of ten to fifty mils, and may contain an antigermicide. Such a coating of beeswax has been found to be effective in preventing the release of fibers of the tampon, while not materially adversely effecting the absorbency or comfort in general to the user of the tampon.

It is accordingly an object of the present invention to provide an improved tampon having a reduced fiber discharge, without loss of absorbency or comfort.

It is another object of the present invention to provide an improved tampon having a special coating which will substantially encapsulate the fibers of the tampon without material sacrifice of absorbency or comfort.

It is another object to provide a tampon that will reduce dryness and abrasion with a resultant enhanced comfort.

It is a further object of the present invention to provide a tampon having a reduced tendency to discharge fibers and, thereby, having a reduced capacity to acquire and transfer bacteria that would otherwise be carried by said fibers.

It is also an object of the invention to provide a tampon that will reduce odors resulting from exotoxins produced by bacteria otherwise capable of holding such exotoxins that are typically held within the fibers of tampons.

The above and yet other objects and advantages of the present invention will become apparent from the hereinafter set forth Detailed Description of the Invention, and Claims appended herewith.

DETAILED DESCRIPTION OF THE INVENTION

A conventional prior art tampon, such as that commercially known as the O.B. Tampon, produced by The Personal Products Company, Milltown, N.J. 08850, consists of a number of spiraled layers of a cotton-rayon material. The present invention is applicable to any tampon made of a fibrous material, regardless of its internal geometry, including, without limitation, those tampons manufactured by Tampex, Playtex and Kotex.

The present invention is practiced by simply dipping, spraying, or otherwise coating the exterior axial circumferential surface of the tampon with a layer, between ten and fifty mils in thickness, of beeswax from the *Apis mellifera* (the European honeybee). Such beeswax may be simply heated, prior to dipping, or may be heated prior to placement into a spray gun type coating device and, thereafter, sprayed onto the circumferential surface of the tampon.

In that beeswax has a relatively low melting point i.e., about 64 degrees Centigrade, it may be readily melted for purposes of such dipping or spraying Also, the fact that beeswax is a soft and pliable material contributes to its workability and, as well, to its comfort to the user of the tampon.

The beeswax of the European honeybee constitutes a composition including numerous complex organic molecules. More particularly, in a study entitled "Beeswax-Composition and Analysis, by Tulloch, National Research Council of Canada", it was concluded that beeswax consists of 14% hydrocarbons, 35% monoesters, 14% diesters, 3% triesters, 4% hydroxy monoesters, 8% hydroxy polyesters, 12% free acids, 1% acid esters, 2% acid polyesters, 1% alcohols, and 6% unidentified. In all, there are more than three hundred individual components of beeswax, however, only four-Carbon40 (6%), Carbon40 (8%) and Carbon48 (6%) monoesters and Carbon24 acid (6%) exceed five percent of the total. The major difunctional component attained upon the hydrolysis of beeswax is 15-hydroxyhexadecanoic acid.

Beeswax of African species has been found to be essentially identical to said *Apis mellifera* from Europe, while Asiatic species have been found to be materially different from the beeswax of *Apis mellifera*.

At present, no inorganic equivalent to beeswax is known in the art.

Also, vegetable waxes and petroleum waxes are not, for purposes of this invention, considered equivalent in that they are lacking in suitable porosity and malleability. The present invention, it is to be appreciated, applies to both the method of coating tampons with beeswax and, as well, the resultant product or structure thereof.

Clinical studies of women using the present inventive tampon have shown the device to be comfortable, without any noticeable loss of absorbency. More particularly, the beeswax coated tampon has proven its ability to absorb its weight (about 11 grams) in blood, just as is the case with prior art tampons. Also, and of key importance, the release of fibers by the inventive tampon, when immersed in water, is less than ten percent than that of prior art devices. Accordingly, the object of providing a low fiber discharge tampon is achieved.

The addition of the coating of beeswax, in effect, functions as a lubricant, in addition to its other benefits such as reduction of the oxygen level within vagina in that untreated fibers are highly porous and all normally carry oxygen therein. Thereby, thru the treatment of fibers, the desired anaerobic state of the vagina can be maintained.

Further, an anti-germicidal agent may be added to the beeswax, or may comprise a pre-coating of the fibers.

Accordingly, while there has been shown and described the preferred embodiment of the present invention, it is to be appreciated that the invention may be embodied otherwise than is herein specifically illustrated and described and that, within the scope of such embodiments, certain changes may be made within the detail and construction of the parts without departing from the underlying idea or principles of this invention within the scope of the appended claims.

Having thus described my invention, of what I claim is new, useful, and non obvious and, accordingly, secured by Letters Patent of the United States is:

1. A method of decreasing the fiber release characteristic of a tampon, comprising the step of:
providing to the tampon a coating of beeswax sufficiently finely distributed upon the surface of the tampon to permit fluid permeability into the tampon.

2. The method as recited in claim 1 in which said coating step further comprises:
the step of coating the axial circumferential surface of the tampon with a layer of beeswax to a thickness of between ten and fifty mils.

3. The method as recited in step 2 in which said coating step comprises:
the dipping of the untreated tampon into liquified beeswax, followed by the removal therefrom, and the drying thereof.

4. The method as recited in claim 2 in which said coating step comprises:
the spraying of the circumferential surface of the untreated tampon with liquified beeswax.

5. A tampon of the type formed of a fiber fabric, in which the improvement comprises:
a coating of beeswax sufficiently finely distributed upon the circumferential surface of said tampon to permit fluid permeability into the tampon.

6. The tampon as recited in claim 5 in which said coating comprises a depth of between ten and fifty mils.

7. The tampon as recited in claim 5 further comprising a pre-coating of the fiber with an anti-germicidal agent.

* * * * *